(12) United States Patent
Nyffeler et al.

(10) Patent No.: US 8,963,684 B2
(45) Date of Patent: *Feb. 24, 2015

(54) GAMMA STERILIZABLE RFID SYSTEM THAT PREVENTS UNAUTHORIZED OPERATION OF ASSOCIATED DISPOSABLE BIOPROCESS COMPONENTS

(75) Inventors: Manuel Nyffeler, Stockholm (SE); Radislav A. Potyrailo, Niskayuna, NY (US); Vincent F. Pizzi, Millis, MA (US); William G. Morris, Rexford, NY (US); Gerard J. Gach, Shrewsbury, MA (US); Vijay Singh, Far Hills, NJ (US)

(73) Assignee: GE Healthcare Bio-Sciences Corp, Piscataway, NJ (US)

( * ) Notice: Subject to any disclaimer, the term of this patent is extended or adjusted under 35 U.S.C. 154(b) by 507 days.

This patent is subject to a terminal disclaimer.

(21) Appl. No.: 12/921,459

(22) PCT Filed: Aug. 20, 2008

(86) PCT No.: PCT/US2008/073624
§ 371 (c)(1),
(2), (4) Date: Sep. 8, 2010

(87) PCT Pub. No.: WO2009/120231
PCT Pub. Date: Oct. 1, 2009

(65) Prior Publication Data
US 2011/0006878 A1   Jan. 13, 2011

Related U.S. Application Data

(60) Provisional application No. 61/039,938, filed on Mar. 27, 2008.

(51) Int. Cl.
*H04Q 9/00* (2006.01)
*G06K 19/07* (2006.01)
(Continued)

(52) U.S. Cl.
CPC ........ *G06K 19/0723* (2013.01); *G06Q 20/3278* (2013.01); *G06Q 20/409* (2013.01); *G11C 11/22* (2013.01)
USPC ............................................. 340/5.8

(58) Field of Classification Search
USPC ..................... 340/5.8, 572.1, 10.1, 603, 606; 235/375, 376
See application file for complete search history.

(56) References Cited

U.S. PATENT DOCUMENTS

| 4,119,946 A | 10/1978 | Taylor |
| 4,502,141 A | 2/1985 | Kuki |

(Continued)

FOREIGN PATENT DOCUMENTS

| CN | 1728162 A | 2/2006 |
| CN | 101122947 A | 2/2008 |

(Continued)

OTHER PUBLICATIONS

Baloda, S., et al., Guide to Irradiation and Sterilization Validation of Single-Use Bioprocess Systems, Part 1, BioProcess International 2007, September, 32-40.

(Continued)

*Primary Examiner* — Vernal Brown

(57) ABSTRACT

This invention provides a system and apparatus that is able to authenticate and prevent illegal manufacturing and unauthorized operation of disposable bioprocess components. This invention utilizes a ferro-electric random access memory (FRAM) chip to store error-correctable information on a RFID tag attached to the disposable bioprocess components, where the error-correctable information is written into the memory chip, so that the information can remain in the chip when the RFID tag and disposable bioprocess component is gamma-sterilized. Also, this invention includes a method for authenticating the disposable bioprocess component that reduces liability in that a counterfeit poor quality disposable component is not used on the hardware so the user will not file an unjustified complaint.

26 Claims, 8 Drawing Sheets

(51) Int. Cl.
   *G06Q 20/32* (2012.01)
   *G06Q 20/40* (2012.01)
   *G11C 11/22* (2006.01)

(56) References Cited

U.S. PATENT DOCUMENTS

| | | | |
|---|---|---|---|
| 4,792,953 | A | 12/1988 | Pasdera et al. |
| 4,852,099 | A | 7/1989 | Ozaki |
| 5,349,558 | A | 9/1994 | Cleveland et al. |
| 5,892,458 | A | 4/1999 | Anderer et al. |
| 7,135,977 | B2 | 11/2006 | Burg et al. |
| 7,195,149 | B2 | 3/2007 | Baker et al. |
| 7,328,837 | B2 | 2/2008 | Baker et al. |
| 8,405,508 | B2 | 3/2013 | Burke |
| 8,653,940 | B2 * | 2/2014 | Nyffeler et al. ............ 340/5.8 |
| 2007/0090926 | A1 | 4/2007 | Potyrailo et al. |
| 2007/0090927 | A1 | 4/2007 | Potyrailo et al. |
| 2007/0224700 | A1 | 9/2007 | Masters |
| 2008/0012577 | A1 | 1/2008 | Potyrailo et al. |
| 2008/0042837 | A1 | 2/2008 | Burke |
| 2009/0256679 | A1 * | 10/2009 | Potyrailo et al. ............ 340/10.1 |

FOREIGN PATENT DOCUMENTS

| | | |
|---|---|---|
| WO | WO 2007/055015 | 5/2007 |
| WO | WO 2008/030659 | 3/2008 |

OTHER PUBLICATIONS

Lehtonen, M., et al., From Identification to Authentication—A Review of RFID Product Authentication Techniques, In Networked RFID Systems and Lightweight Cryptography. Raising Barriers to Product Counterfeiting; P. H. Cole and D. C. Ranasinghe, Ed.; Springer: Berlin Heidelberg, 2008; 169-187.

Strauss, K., et al., Overview of radiation tolerant unlimited write cycle non-volatile memory, IEEE Aerospace Conf. Proc. 2000, 5, 399-408.

Unofficial English translation of Office Action issued in connection with corresponding CN Application No. 200880128544.9 on Mar. 6, 2013.

* cited by examiner

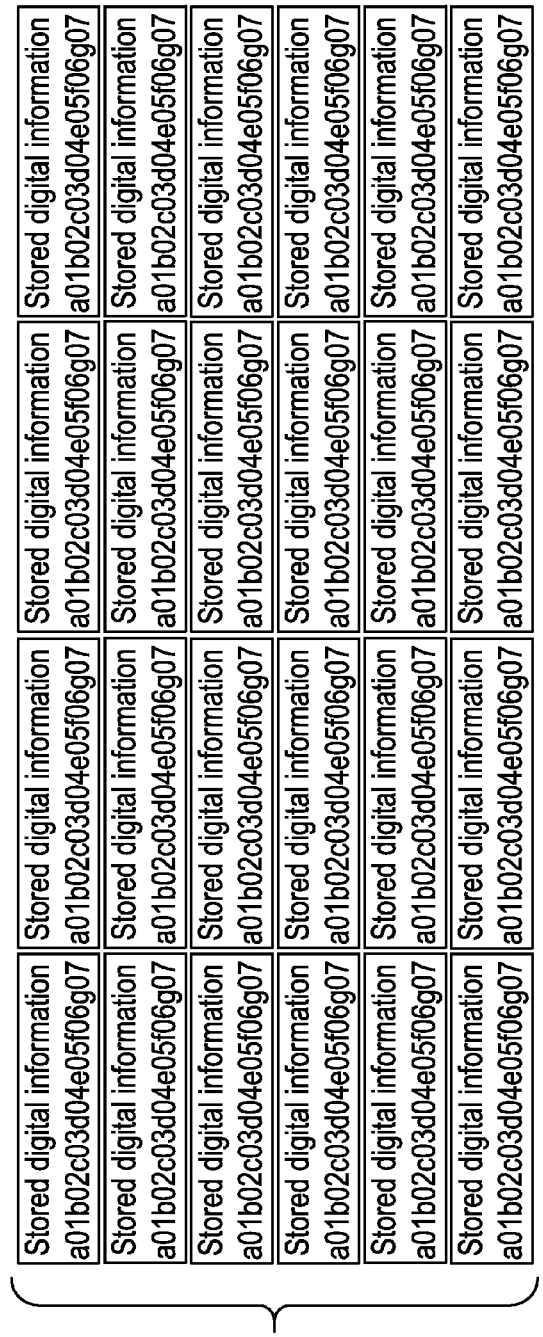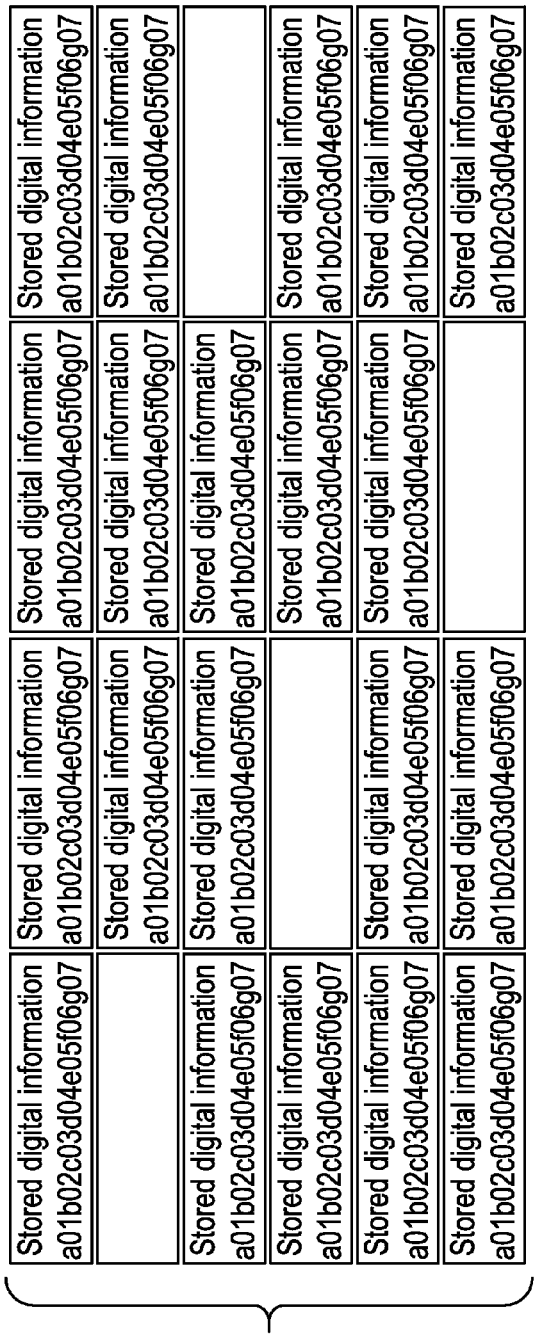
FIG. 4A
FIG. 4B

FIG. 8

A / B / C = Unencrypted data / Encrypted data / Empty (no data)

| Red Tags | MB89R118A Page Redundancy | Memory = Read After Irradiation | 2000 Bytes Pages with errors | 25 pages of Able to Validate Data | 80 bytes Write After Irradiation | Pass |
|---|---|---|---|---|---|---|
| Tag No. | A / B / C | A / B / C | A / B / C | A / B / C | | |
| 1 | 11 / 9 / 5 | 10 / 9 / 5 | 1 / 0 / 0 | Y / Y / Y | Yes | Yes |
| 2 | 11 / 9 / 5 | 11 / 9 / 5 | 0 / 0 / 0 | Y / Y / Y | Yes | Yes |
| 3 | 11 / 9 / 5 | 11 / 9 / 5 | 0 / 0 / 0 | Y / Y / Y | Yes | Yes |
| 4 | 11 / 9 / 5 | 11 / 9 / 5 | 0 / 0 / 0 | Y / Y / Y | Yes | Yes |
| 5 | 11 / 9 / 5 | 11 / 9 / 5 | 0 / 0 / 0 | Y / Y / Y | Yes | Yes |
| 6 | 11 / 9 / 5 | 11 / 9 / 5 | 0 / 0 / 0 | Y / Y / Y | Yes | Yes |
| 7 | 11 / 9 / 5 | 11 / 9 / 5 | 0 / 0 / 0 | Y / Y / Y | Yes | Yes |
| 8 | 11 / 9 / 5 | 11 / 9 / 5 | 0 / 0 / 0 | Y / Y / Y | Yes | Yes |
| 9 | 11 / 9 / 5 | 11 / 9 / 5 | 0 / 0 / 0 | Y / Y / Y | Yes | Yes |
| 10 | 11 / 9 / 5 | 11 / 9 / 5 | 0 / 0 / 0 | Y / Y / Y | Yes | Yes |
| 11 | 11 / 9 / 5 | 11 / 9 / 5 | 0 / 0 / 0 | Y / Y / Y | Yes | Yes |
| 12 | 11 / 9 / 5 | 11 / 9 / 5 | 0 / 0 / 0 | Y / Y / Y | Yes | Yes |
| 13 | 11 / 9 / 5 | 11 / 9 / 5 | 0 / 0 / 0 | Y / Y / Y | Yes | Yes |

GAMMA STERILIZABLE RFID SYSTEM THAT PREVENTS UNAUTHORIZED OPERATION OF ASSOCIATED DISPOSABLE BIOPROCESS COMPONENTS

CROSS-REFERENCE TO RELATED APPLICATIONS

This application is a filing under 35 U.S.C. §371 and claims priority to international patent application number PCT/US2008/073624 filed Aug. 20, 2008, published on Oct. 1, 2009, as WO 2009/120231, which claims priority to U.S. provisional patent application No. 61/039,938 filed on Mar. 27, 2008; the disclosure of which is incorporated herein by reference in its entirety.

FIELD OF THE INVENTION

This invention relates to a radio frequency identification system that detects illegal manufacturing and prevents unauthorized operation of disposable bioprocess components

BACKGROUND OF THE INVENTION

Radio frequency identification (RFID) tags are widely employed for automatic identification of objects, such as animals, garments etc. and detection of unauthorized opening of containers. There are several examples of RFID tags being used to identify objects.

First, there is a U.S. Pat. No. 7,195,149 for a method of attaching an RFID tag to a hose and tracking system. This hose tracking system includes a hose assembly with an attached RFID tag embedded therein during manufacture, molded thereon permanently attached. The RFID tag is coded with an identification specific to the particular hose assembly. An RFID tag reader is provided, which is usable by a user to obtain the identification from the RFID tag on the hose, preferably after it is installed at the user facility. The RFID tag reader includes a user input for at least one trackable event and is at least connectable to a computer network or compatible for uploading the identification and any user input to a network accessible device. A network accessible hose database is provided, having hose-related information. The network accessible hose database provides access to a user to obtain the hose-related information based on the identification from the RFID tag that receives and stores data related to the at least one trackable event. There is also another U.S. Pat. No. 7,328,837 similar to U.S. Pat. No. 7,195,149, where U.S. Pat. No. 7,328,837 is for a method of attaching an RFID tag to a hose and tracking system.

Next, there is U.S. Pat. No. 5,892,458 that is an apparatus for the recognition of exchangeable parts in analytical measuring instruments. The apparatus for the recognition of exchangeable parts in an analytical measuring instrument or in an analytical measurement system with several analytical devices contain exchangeable parts that have identification modules that are each attached to an exchangeable part. In addition, the apparatus has transmitter receiver devices that can receive information signals from an identification module and send information signals to the identification module. The control device can cause a message to be displayed on a display device if the information read out from an identification module does not fulfill certain conditions, for example with regard to the quality.

Next, there is another U.S. Pat. No. 7,135,977 for a method and system for tracking identification devices, which includes storing data about the identification device in a register, the data to be stored including data relating to a forwarding location that requests information about the identification device should be forwarded. The identification device is attached to an item to be monitored. The method includes accessing the register when the identification device has been read and a request for information has been received. Details of the forwarding location are obtained from the register. The request is forwarded to the forwarding location and the requested information about the identification device is sent from the forwarding location to a requester of the information.

While the aforementioned RFID inventions have been able to identify devices associated with the RFID tags, these inventions are not able to authenticate and prevent illegal manufacturing and unauthorized operation of gamma sterilizable disposable bioprocess components. Therefore, there is a need for an apparatus and system that is able to authenticate and prevent illegal manufacturing of disposable bioprocess components, especially those that are sterilized by gamma irradiation or other suitable means of lowering bio-burden of the disposable or limited reuse device.

BRIEF SUMMARY OF THE INVENTION

The present invention has been accomplished in view of the above-mentioned technical background, and it is an object of the present invention to provide a system and method for authenticating disposable bioprocess components attached to RFID tags.

In a preferred embodiment of the invention, there is a method for preventing an unauthorized use of a disposable bioprocess component. The method includes: fabricating an RFID tag and a disposable component; integrating the RFID tag with the disposable component; initializing the memory chip by applying RF signal to the complementary metal-oxide semiconductor (CMOS) circuitry; writing error-correctable information to a ferroelectric random memory (FRAM) portion part of a memory chip of the RFID tag; sterilizing the disposable component with the integrated RFID tag; assembling the disposable component in a biological fluid flow; detecting and correcting possible errors in written data caused by gamma irradiation; and determining if the disposable bioprocess component is authenticated.

In a preferred embodiment of the invention, there is a method for preventing an unauthorized use of a disposable bioprocess component. The method includes: fabricating an RFID tag and a disposable component; integrating the RFID tag with the disposable component; initializing the memory chip by applying RF signal to the complementary metal-oxide semiconductor (CMOS) circuitry and writing error-correctable information to a plurality of regions on a ferroelectric random memory (PRAM) portion part of a memory chip of the RFID tag; sterilizing the disposable component with the integrated RFID tag; assembling the disposable component in a biological fluid flow; and determining if the disposable bioprocess component is authenticated.

In another preferred embodiment of the invention, there is a method for preventing an unauthenticated use of a disposable bioprocess component. The method includes: integrating an RFID tag with a disposable component; writing error-correctable information on a Ferro-electric random access memory (FRAM) chip of the RFID tag; sterilizing the disposable bioprocess component with the integrated RFID tag; assembling the disposable component in a biological fluid flow; determining the information on the RFID tag in the disposable bioprocess component; determining if the disposable bioprocess component is authenticated; and releasing digital data on the RFID tag if the information on the RFID tag in the disposable bioprocess component is authenticated.

In yet another preferred embodiment of the invention, there is a method for preventing an unauthorized use of a disposable bioprocess component with the RFID tag where the memory of the memory chip of the tag has a maximum available data capacity. The method includes: fabricating an RFID tag that includes a memory chip that contains both a CMOS circuitry and a FRAM circuitry; fabricating a disposable bioprocess component; integrating the RFID tag with the disposable bioprocess component; initializing the memory chip by applying RF signal to the CMOS circuitry and writing redundant information to a plurality of regions in the FRAM circuitry of the memory chip of the RFID tag; sterilizing the disposable bioprocess component with the integrated RFID tag; assembling the disposable bioprocess component in a biological fluid flow; authenticating the disposable bioprocess component with the RFID tag; and releasing the available memory from the redundant memory blocks to the end-user.

In another embodiment of the invention, there is a method for preventing an unauthorized use of a disposable bioprocess component with an RFID tag where the memory chip of the tag has the radiation-hardened CMOS structure of the memory chip and a non-volatile memory. The method includes: fabricating an RFID tag with a memory chip that contains both a radiation-hardened CMOS circuitry and a FRAM circuitry, fabricating a disposable bioprocess component; integrating the RFID tag with the disposable bioprocess component; initializing the memory chip by applying RF signal to the radiation-hardened CMOS circuitry and writing redundant information to a plurality of regions in FRAM part of the memory chip of the RFID tag; sterilizing the disposable bioprocess component with the integrated RFID tag; assembling the disposable bioprocess component in a biological fluid flow vessel or purification component; and authenticating the disposable bioprocess component with the RFID tag.

In another embodiment of the invention, there is a method for preventing an unauthorized use of a disposable bioprocess component with an RFID tag that contains both a CMOS circuitry and a FRAM circuitry. The method includes: fabricating an RFID tag with a memory chip that contains both a CMOS circuitry and a FRAM circuitry, fabricating a disposable bioprocess component; integrating the RFID tag with the disposable bioprocess component; initializing the memory chip by applying RF signal to the CMOS circuitry and writing redundant information to a plurality of regions in FRAM part of the memory chip of the RFID tag; gamma-sterilizing the disposable bioprocess component with the integrated RFID tag; assembling the disposable bioprocess component in a biological fluid flow; recovering the CMOS circuitry after the gamma irradiation, and authenticating the disposable bioprocess component with the RFID tag.

In yet another embodiment of the invention, there is a method for preventing an unauthorized use of a disposable bioprocess component with an RFID tag that has a memory chip that contains both a CMOS circuitry and a FRAM circuitry of the RFID memory chip. The method includes: fabricating an RFID tag that includes a memory chip that contains both a CMOS circuitry and a FRAM circuitry, fabricating a disposable bioprocess component; integrating the RFID tag with the disposable bioprocess component; initializing the memory chip by applying RF signal to the CMOS circuitry and writing redundant information to a plurality of regions in FRAM part of the memory chip of the RFID tag, where writing of redundant information to a plurality of regions in FRAM part of the memory chip of the RFID tag is accomplished by sending information only once to the RFID tag and sending the number of desired redundancy; and the memory chip configured to write redundant information into memory blocks; sterilizing the disposable bioprocess component with the integrated RFID tag; assembling the disposable bioprocess component in a biological fluid flow; reading of redundant information from a plurality of regions in FRAM part of the memory chip of the RFID tag, where reading is done from the redundant memory blocks and comparing the information from redundant blocks, and releasing only the most redundant information; and authenticating the disposable bioprocess component with the RFID tag.

In yet another embodiment of the invention, there is a method for preventing an unauthorized use of a disposable bioprocess component. The method includes: fabricating an RFID tag that includes a memory chip that contains both a CMOS circuitry and a FRAM circuitry, fabricating a disposable bioprocess component; integrating the RFID tag with the disposable bioprocess component; initializing the memory chip by applying RF signal to the CMOS circuitry and writing error-correctable information to FRAM part of the memory chip of the RFID tag, encrypting the information; sterilizing the disposable bioprocess component with the integrated RFID tag; assembling the disposable bioprocess component in a biological fluid flow; decrypting information; and authenticating the disposable bioprocess component with the RFID tag.

In another embodiment of the invention, there is a method for preventing an unauthorized use of a disposable bioprocess component. The method includes: fabricating an RFID tag that includes a memory chip that contains both a CMOS circuitry and a FRAM circuitry, fabricating a disposable bioprocess component; adapting the RFID tag for physical, chemical, or biological sensing in disposable bioprocess component; integrating the resulting RFID sensor with the disposable bioprocess component; initializing the memory chip by applying RF signal to the CMOS circuitry and writing error-correctable information to FRAM part of the memory chip of the RFID sensor where information contains calibration parameters of the sensor; sterilizing the disposable bioprocess component with the integrated RFID sensor; assembling the disposable bioprocess component in a biological fluid flow; and authenticating the disposable bioprocess component with the RFID sensor.

In another embodiment of the invention, there is a method for preventing an unauthorized use of a disposable bioprocess component. The method includes: fabricating an RFID tag that includes a memory chip that contains a CMOS circuitry, a FRAM circuitry, and analog input from a physical, chemical, or biological sensor, attaching at least one physical, chemical, or biological sensor to the memory chip, fabricating a disposable bioprocess component; integrating the resulting RFID sensor with the disposable bioprocess component; initializing the memory chip by applying RF signal to the CMOS circuitry and writing error-correctable information to a plurality of regions in FRAM part of the memory chip of the RFID sensor where information contains calibration parameters of the sensor; sterilizing the disposable bioprocess component with the integrated RFID sensor; assembling the disposable bioprocess component in a biological fluid flow; and authenticating the disposable bioprocess component with the RFID sensor where authentication involves RFID sensor initialization and a change of its reading.

In another embodiment of the invention, there is a method for preventing an unauthorized use of a disposable bioprocess component with an RFID tag that contains both a CMOS circuitry and a FRAM circuitry. The method includes: fabricating an RFID tag with a memory chip that contains both a CMOS circuitry and a FRAM circuitry, fabricating a disposable bioprocess component; integrating the RFID tag with the disposable bioprocess component; initializing the memory chip by applying RF signal to the CMOS circuitry and writing error-correctable information to FRAM part of the memory chip of the RFID tag; gamma-sterilizing the disposable bioprocess component with the integrated RFID tag; assembling the disposable bioprocess component in a biological fluid flow, and authenticating the disposable bioprocess component with the RFID tag when RFID tag reading is performed at different power levels of the RFID tag reader or at different distances between the reader and the RFID tag.

BRIEF DESCRIPTION OF THE DRAWINGS

These and other advantages of the present invention will become more apparent as the following description is read in conjunction with the accompanying drawings, wherein:

FIGS. 4A and 4B depict a block diagram of redundant information stored in the RFID chip of FIG. 2 in accordance with an embodiment of the invention;

FIG. 8 illustrates a table of how the RFID tag operates in accordance with an embodiment of the invention.

DETAILED DESCRIPTION OF THE INVENTION

The presently preferred embodiments of the invention are described with reference to the drawings, where like components are identified with the same numerals. The descriptions of the preferred embodiments are exemplary and are not intended to limit the scope of the invention.

Figure 1:
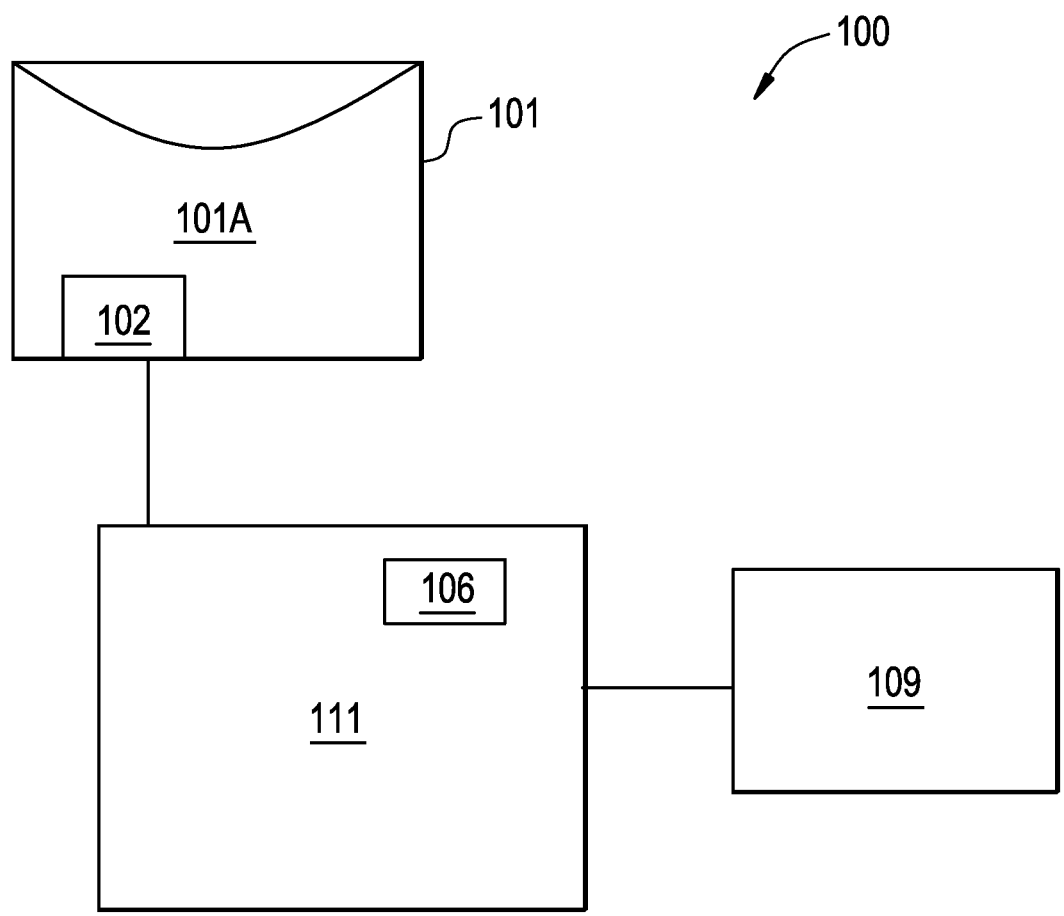
FIG. 1 illustrates a block diagram of a system in accordance with an embodiment of the invention.

FIG. 1 illustrates a block diagram of a system for measuring parameters in a container. The system 100 includes a container 101, a radio frequency identification (RFID) tag 102, a standard computer 109 and a measurement device (writer/reader) 111, which includes a reader 106. The tag 102 is incorporated or integrated into the container 101. RFID tag 102 may also be referred to as tag 102.

Container 101 may be a disposable bio-processing container, a cell culture bioreactor, a mixing bag, a sterilization container, a metal container, a plastic container, a polymeric material container, a chromatography device, a filtration device, a chromatography device with any associated transfer conduits, a filtration device with any associated transfer conduits, centrifuge device, a connector, a fitting, a centrifuge device with any associated transfer conduits, a pre-sterilized polymeric material container or any type of container known to those of ordinary skill in the art. In one embodiment, the biological container 101 is preferably made from but not limited to the following materials, alone or in any combination as a multi-layer film: ethylene vinyl acetate (EVA) low or very low-density polyethylene (LDPE or VLDPE) ethyl-vinyl-alcohol (EVOH) polypropylene (PP), polyethylene, low-density polyethylene, ultra-low density polyethylene, polyester, polyamid, polycarbonate, fluoropolymers such as Fluorinated ethylene propylene (FEP) (made by E. I. du Pont de Nemours and Company located in Wilmington, Del.) and Polyvinylidene Fluoride (PVDF), elastomeric materials all of which are well known in the art. A RFID tag typically comprises an antenna and a microchip with a plastic backing (e.g., polyester, polyimide etc).

Also, the container 101 may be made of a multilayer bioprocessing film, made from one manufacturer. For example, the manufacturer may be GE Healthcare, located in Somerset, N.J., Piscataway, N.J., Westborough, Mass., Newport or Millipore in Calif. or Mass., or Hyclone located in Logan, Utah, for example HyQ® CX5-14 film and HYQ® CX3-9 film. The CX5-14 film is a 5-layer, 14 mil cast film. The outer layer of this film is made of a polyester elastomer coextruded with an EVOH barrier layer and an ultra-low density polyethylene product contact layer. The CX3-9 film is a 3-layer, 9 mil cast film. The outer layer of this film is a polyester elastomer coextruded with an ultra-low density polyethylene product contact layer. The aforementioned films may be further converted into disposable bio-processing components in a variety of geometries and configurations all of which can hold a solution 101a. In yet another embodiment of the invention, the container 101 may be a polymer material incorporated into a filtration device. Further, the container 101 may include or contain a chromatographic matrix.

Depending on the material of the container, the RFID tag 102 is connected by a wireless connection to the measurement device (writer/reader) 111 and the computer 109. Container 101 may also be a vessel that contains a fluid such as liquid or gas, where the vessel can have an input and an output. Further, container 101 can have a liquid flow or no liquid flow. Furthermore, container 101 can be a bag, a tube, or a pipe, or a hose.

Figure 2:
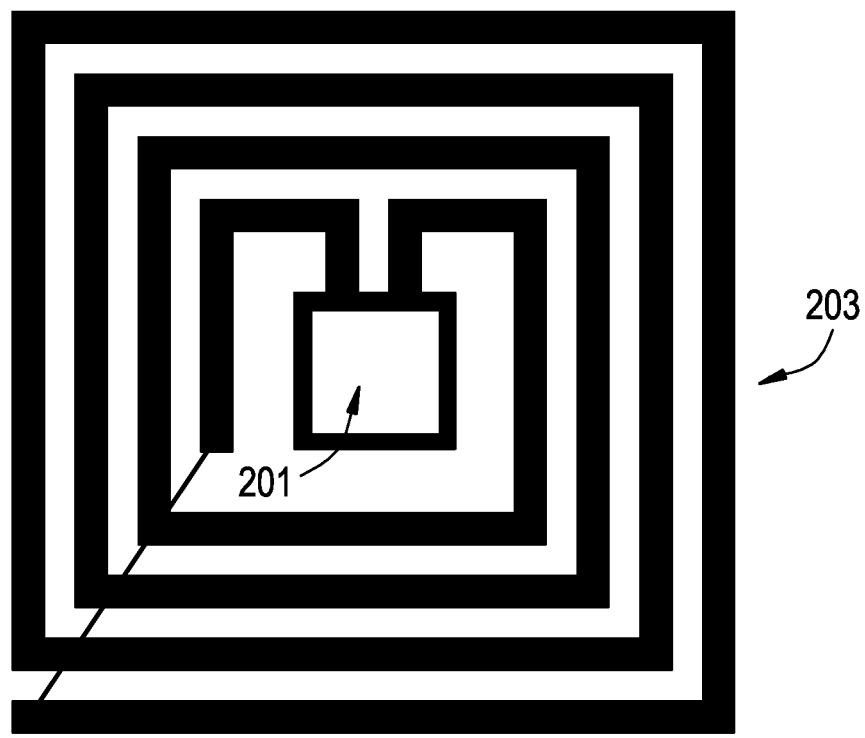
FIG. 2 shows a radio frequency identification (RFID) tag of FIG. 1 in accordance with an embodiment of the invention.

FIG. 2 is the RFID tag 102. RFID tag 102 is gamma radiation resistant to typical levels required for pharmaceutical processing (25 to 50 kGy). The gamma radiation. resistance (immunity to effects of gamma radiation) is provided in several ways and that are used in combination or separately: 1. from the storage of required digital information that allows its error correction; 2. from the use of radiation-hardened CMOS circuitry on RFID tag or from control of recovery of the standard CMOS after gamma irradiation; 3. from the use of FRAM memory; and 4. from the reading of the RFID tag after gamma radiation with different power levels of the reader or at different distances between the reader and the RFID tag. The first component of the RFID tag 102 is an integrated circuit memory chip 201 for storing and processing information and modulating and demodulating a radio frequency signal. Also, memory chip 201 can also be used for other specialized functions, for example it may contain a capacitor. It may also contain an input for an analog signal. A second component for this RFID tag 102 is an antenna 203 for receiving and transmitting the radio frequency signal.

Storage of required digital information that allows the error correction of this information is done by using known methods. Non-limiting examples of these methods include redundancy, Reed-Solomon error correction (or code), Hamming error correction (or code), BCH error correction (or code), and others known in the art.

Figure 3:
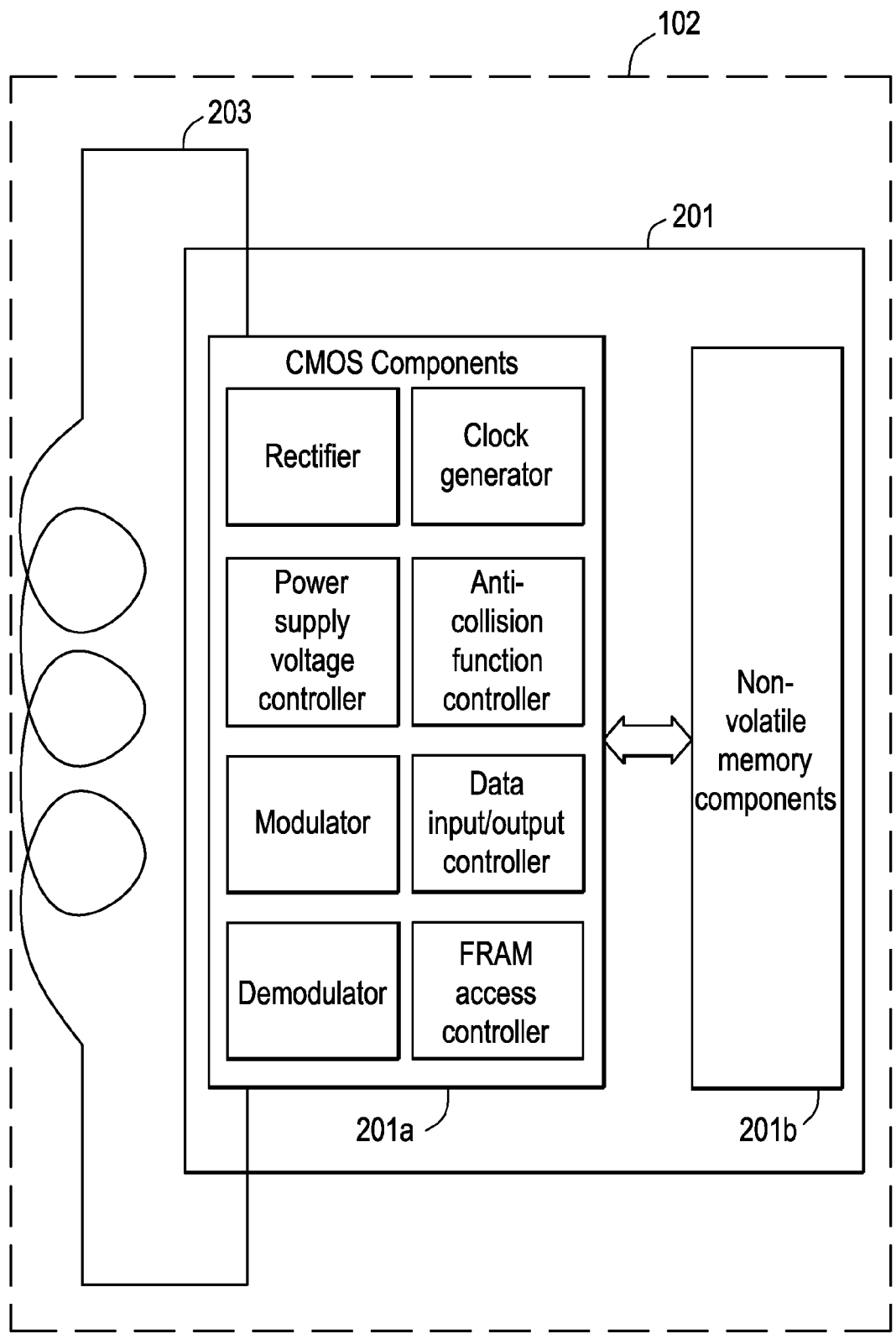
FIG. 3 illustrates a schematic of a memory chip of the RFID tag of FIG. 1 in accordance with an embodiment of the invention.

Data redundancy is achieved by writing multiple copies of the data into memory so as to protect them from memory faults. Writing multiple copies of the data into the memory or writing redundant information on a FRAM chip 201b (FIG. 3)

of the RFID tag 102 means writing information into plurality of regions on the memory chip. The goal of writing redundant information on a FRAM chip of the RFID tag is to reduce gamma irradiation effect that otherwise can cause loss of at least portion of data that will lead to the failure to authenticate a disposable bioprocess component attached to the RFID tag.

The Reed-Solomon error correction is the method used for detecting and correcting errors as described in U.S. Pat. Nos. 4,792,953 and 4,852,099. This error correction method was used for example, in compact disks and digital video disks. In order to detect and correct errors in data from RFID tags, the data to be written is converted into Reed-Solomon codes by a computer algorithm and the codes are written to the RFID memory. When the codes are read back from the RFID memory, they are processed through a computer algorithm that detects errors, uses the information within the codes to correct the errors, and reconstructs the original data.

The Hamming error correction has been used in random access memory (RAM), programmable read-only-memory (PROM) or read-only-memory as detailed in U.S. Pat. No. 4,119,946. By using the Hamming error correction to RFID memory, the data to be stored in RFID memory is processed by an algorithm where it is divided into blocks, each block is transformed to a code using a code generator matrix, and the code is written to the RFID memory. After the code has been read back from the RFID memory, it is processed by an algorithm that includes a parity-check matrix that can detect single-bit and double-bit errors, but only the single bit errors can be corrected.

The BCH (Bose-Chaudhuri-Hocquenghem) error correction is a polynomial code over a finite field with a particularly chosen generator polynomial, see for example U.S. Pat. No. 4,502,141. The data to be stored in RFID memory is transformed to a code by using an algorithm based on a generator polynomial, and the code is written to the RFID memory. After the code has been read back from the RFID memory, it is processed by an algorithm that includes calculating roots of a polynomial to locate and correct errors. The Reed-Solomon code can be considered a narrow-sense BCH code.

Referring to FIG. 3, the memory chip 201 includes a complementary metal-oxide semiconductor (CMOS) chip 201$a$ with a ferroelectric random access memory (FRAM) 201$b$.

Memory chip 201 includes the (CMOS) chip or CMOS circuitry 201$a$ and the FRAM circuitry 201$b$ as a part of the RFID tag 102 incorporated into a disposable bioprocess component 101 and preventing its unauthorized use. The examples of the CMOS circuitry 201$a$ components include a rectifier, a power supply voltage control, a modulator, a demodulator, a clock generator, and other known components.

The memory chip 201 that includes a CMOS circuitry and a digital FRAM circuitry is called here "FRAM memory chip". In order to achieve ability to use the memory chip 201 device of an RFID tag 102 for authentication of a gamma-sterilized disposable bioprocess component 101, it is critical to address: (1) limitations of the non-volatile memory material such as ferroelectric memory material and any other non-charge-based storage memory MATERIAL and (2) limitations of the CMOS circuitry 201$a$ of the memory chip 201 as a whole DEVICE upon exposure to gamma radiation.

In general, here are examples of non-volatile memory that are applicable for the purpose of this invention are Giant Magneto-Resistance Random Access Memory (GMRAM), Ferroelectric Random Access Memory (FRAM), and Chalcogenide Memory (GM) as described in Strauss, K. F.; Daud, T., Overview of radiation tolerant unlimited write cycle non-volatile memory, *IEEE Aerospace Conf. Proc.* 2000, 5, 399-408, which is hereby incorporated by reference.

Here are examples of materials that can be used to create ferroelectric memory include potassium nitrate ($KNO_3$), lead zirconate titanate ($PbZr_{1-x}Ti_xO_3$, usually abbreviated as PZT), $Pb_5Ge_3O_{11}$, $Bi_4Ti_3O_{12}$, $LiNbO_3$, $SrBi_2Ta_2O_9$, and others. In ferroelectric memory, the ferroelectric effect is characterized by the remnant polarization that occurs after an electric field has been applied. The unique chemical atomic ordering of ferroelectric materials allows a center atom in the crystal lattice to change its physical location. The center atom in a cubic PZT perovskite crystal lattice will move into one of the two stable states upon an external applied electric field. After the external electric field is removed, the atom remains polarized in either state; this effect is the basis of the ferroelectric as a nonvolatile memory. An electric field can reverse the polarization state of the center atom, changing from a logic state "0" to "1" or vice versa. This nonvolatile polarization, which is the difference between the relaxed states (the charge density) is detected by the detector circuitry. FRAM is a type of memory that uses a ferroelectric material film as a dielectric of a capacitor to store RFID data. On the material level, it is well known that while FRAM is more gamma radiation resistant than EEPROM (Electrically Erasable Programmable Read-Only Memory), it still experiences gamma-irradiation effects. The common gamma radiation sources are cobalt-60 ($Co^{60}$) and cesium-137 ($Cs^{137}$) isotopes. The cobalt 60 isotope emits gamma rays of 1.17 and 1.33 MeV. The cesium 137 isotope emits gamma rays of 0.6614 MeV. This energy of the gamma radiation for the $Co^{60}$ and $Cs^{137}$ sources is high enough to potentially cause displacement damage in the ferroelectric material. Indeed, after an exposure to a gamma radiation, FRAM experiences the decrease in retained polarization charge due to an alteration of the switching characteristics of the ferroelectric due to changes in the internal fields. This radiation-induced degradation of the switching characteristics of the ferroelectric is due to transport and trapping near the electrodes of radiation-induced charge in the ferroelectric material. Once trapped, the charge can alter the local field around the dipoles, altering the switching characteristics as a function of applied voltage. Two known scenarios for trap sites are at grain boundaries or in distributed defects in the ferroelectric material, depending on the fabrication method of FRAM (for example, sputtering, sol-gel deposition, spin-on deposition, metal-organic chemical vapor deposition, liquid source misted chemical deposition). In addition to the charge trapping, gamma radiation can also directly alter the polarizability of individual dipoles or domains.

On the device level, the FRAM memory chip 201 of the RFID tag 102 consists of a standard electric CMOS circuit 201$a$ and an array of ferroelectric capacitors in which the polarization dipoles are temporarily and permanently oriented during the memory write operation of the FRAM. On the device level, the FRAM device has two modes of memory degradation that include functional failure and stored data upset. Thus, the radiation response effect in the memory chip 201 is a combination of non-volatile memory 201$b$ and the CMOS 201$a$ components in the memory chip 201. Radiation damage in CMOS 201$a$ includes but is not limited to the threshold voltage shift, increased leakage currents, and short-circuit latch up.

In conventional CMOS/FRAM memory devices, the gamma radiation induced loss of device performance (the ability to write and read data from the memory chip) is dominated by the unhardened commercial CMOS components of memory chip 201.

Hardened-by-design techniques can be used to manufacture a radiation-hardened CMOS components of semiconductor memory. The examples of hardened-by-design CMOS components include p-channel transistors in memory array, annular n-channel gate structures, p-type guard rings, robust/redundant logic gates protecting latches, latches immune to single event effects (SEE), and some others. The hardened-by-design techniques prevent radiation-hard latches from being set by single event transients (SET) propagating through the logic of the device.

Referring to FIGS. 4A and 4B, shows a block diagram of the redundant information storage is shown. When the same or redundant information is written and stored in different regions as shown in FIG. 4A, while some information may be lost as shown in FIG. 4B after gamma radiation sterilization. After the irradiation of the memory chip 201, the method for redundant information storage provides a reliable storage of the information in at least one remaining non-damaged regions of the FRAM memory chip 201. FRAM is a non-volatile memory 201b offering high-speed writing, low power consumption and long rewriting endurance. The non-limiting examples of memory chips 201 include FRAM chips for 13.56 MHz such as of the FerVID family™ and are MB89R111 (ISO14443, 2 Kbyte), MB89R118 (ISO15693, 2 Kbyte), MB89R119 (ISO15693, 256 byte) available from Fujitsu located at 1250 East Argues Avenue, Sunnyvale, Calif. 94085.

A list of companies that can fabricate FRAM memory chips includes Ramtron International Corporation (Colorado Springs, Colo.), Fujitsu (Japan), Celis Semiconductor (Colorado Springs, Colo.), and others. The RFID tag 102 that contains the FRAM memory chip can also be converted into RFID sensor as described in U.S. patent application numbers US 2007-0090926, US 2007-0090927, and US 2008-0012577 which are hereby incorporated by reference.

Figure 5:
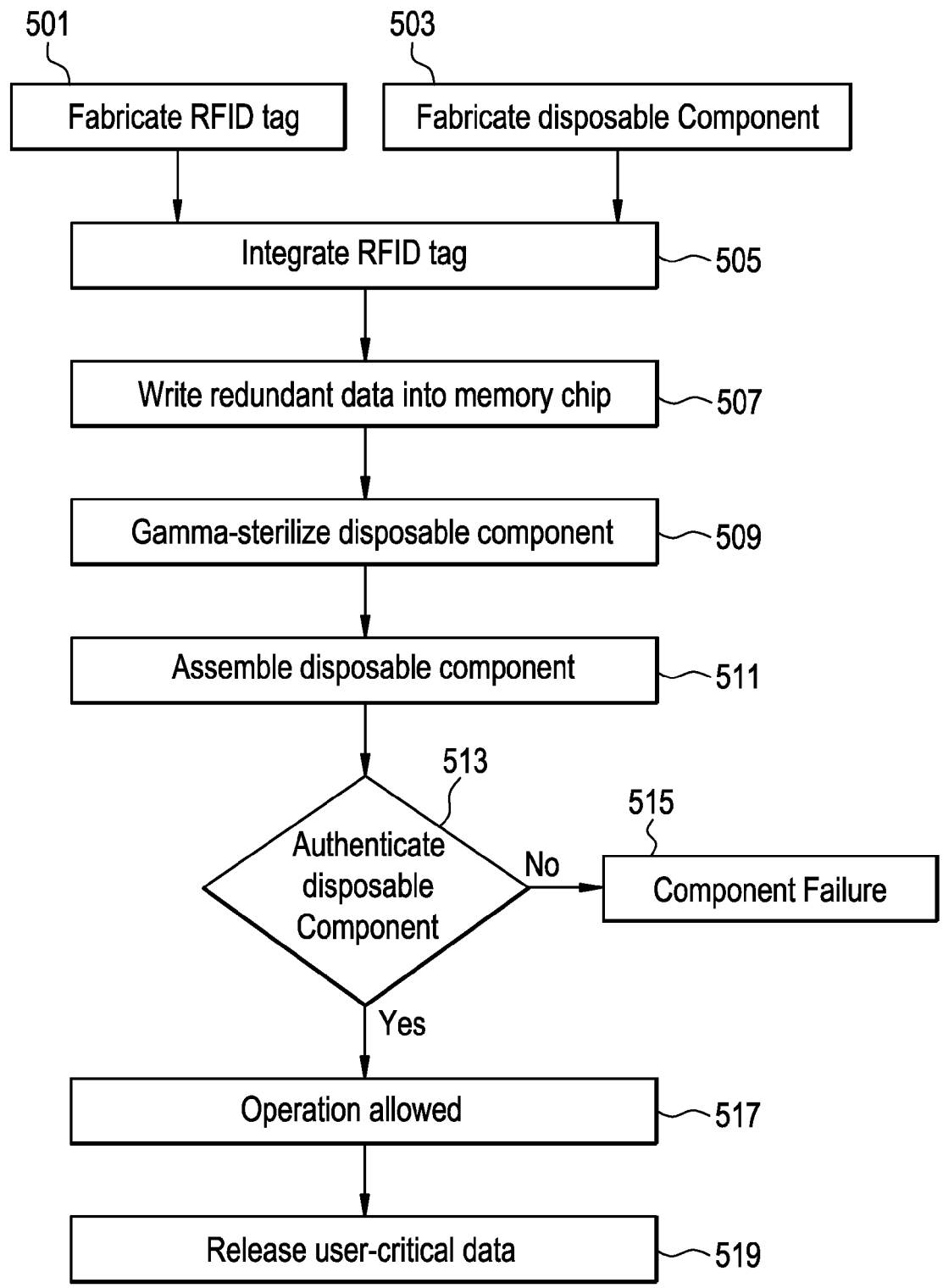
FIG. 5 depicts a flow-chart of the operation of a disposable component with the (RFID) tag of FIG. 1 in accordance with an embodiment of the invention.

FIG. 5 is a flow chart of the operation of the disposable component with the integrated RFID tag 102. At block 501, the RFID tag 102 is fabricated. RFID tag 102 is fabricated in three steps that include: fabrication of a FRAM memory chip 201 (FIG. 2), fabrication of antenna 203, and attachment of memory chip 201 to antenna 203 using acceptable common or typical practices and manufacturing approaches for fabrication known to those of ordinary skill in the art. At block 503, the disposable bioprocess component 101 is fabricated by the typical practices known to those of ordinary skill in the art for fabricating the bioprocess component 101. As stated above, the bioprocess component 101 may be for example, storage bags, bioreactors, transfer lines, filters, separation columns, connectors, and other components. Each of these and other components is fabricated using acceptable common practices and manufacturing approaches known to those of ordinary skill in the art.

After the RFID tag 102 and the disposable bioprocess component 101 are fabricated, then at block 505 the RFID tag 102 is integrated in combination with the disposable bioprocess component 101. RFID tag 102 is integrated in combination with the disposable bioprocess component by using the method known to those of ordinary skill in the art of lamination or molding the RFID tag 102 into the part of the disposable bioprocess component 101 or attaching the RFID tag 102 to the disposable bioprocess component 101. Also, there are other known ways to integrate RFID tags 102 into disposable bioprocess component 101.

Figure 6:
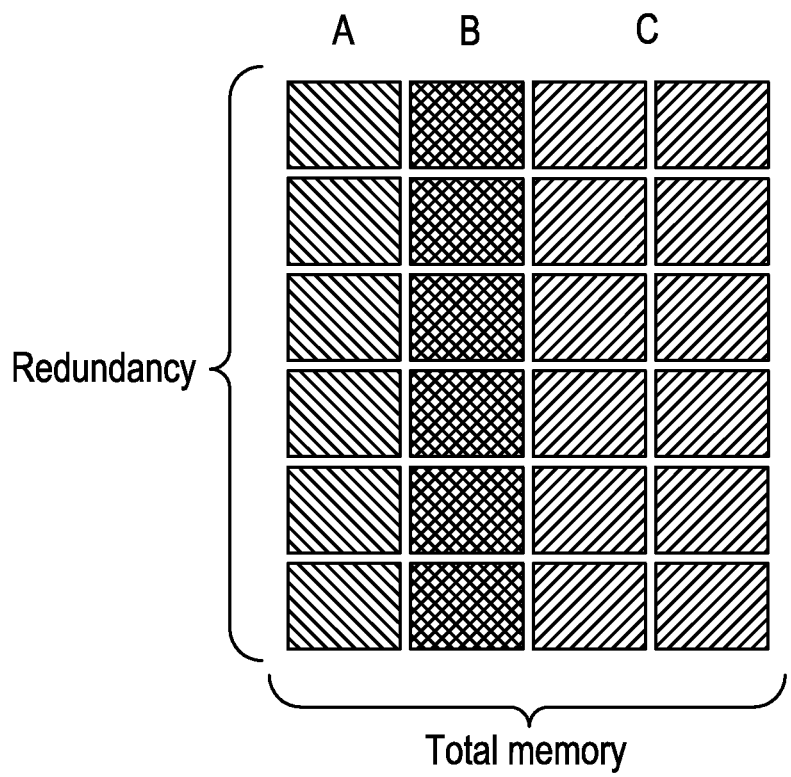
FIG. 6 illustrates the memory chip of FIG. 3 divided into sectors in accordance with an embodiment of the invention.

At block 507, the redundant data is written onto the memory chip 201 of the RFID tag 102. The approach to writing redundant data onto the memory chip 301 is illustrated in FIG. 6, which improves the reliability of writing and reading data onto gamma radiation resistant RFID tags. For this approach, the total available memory of the memory chip 201 is divided into three sectors: sector A for article identification (ID) information, serial number and possible sensor calibrations, sector B for authentication information and sector C with user available blocks. Sector A may be referred to as a first sector, sector B may be referred to as a second sector and sector C may be referred to as a third sector. Even though, there is only one memory chip 201 depicted here a plurality of memory chips may be utilized, for example 1 to 100 memory chips, included in one or more RFID tags. Also, even though this memory chip 201 only has three sectors the memory chip may have 1 to 100 or more sectors.

The redundant data is written into each sector A, B and C. Redundancy is achieved by writing multiple copies of the data into each sector A, B and C.

Referring to FIG. 8, there is a table illustrating how the redundant information is stored on sectors A, B and C. For example, the improvement of reliability of writing and reading data onto RFID tags after their gamma irradiation was demonstrated using memory chips MB89R118A (Fujitsu). These memory chips are made using a standard 0.35 micrometers CMOS circuitry process coupled with a process of manufacturing ferroelectric memory. These memory chips were attached to 5.5×8.5 cm antenna. Writing and reading of data was performed using a computer-controlled multi-standard RFID Reader/Writer evaluation module (Model TRF7960 Evaluation Module, Tex. Instruments) and a reader/writer 111 from Wave Logic LLC (Scotts Valley, Calif.).

The total available 2000 bytes memory of memory chips was divided into three sectors such as a sector A for article ID, serial number, and possible sensor calibrations, sector B for authentication, and sector C with user available blocks. Redundant data was written into two sectors (A and B). The sectors A, B, and C were unencrypted data, encrypted data, and empty (no data), respectively. The respective page redundancy was 11, 9, and 5, thus we had 25 pages (11+9+5=25) of 80 bytes per page. The goal was to write redundant data, gamma irradiate the tags, read the data back, and count the number of pages that were correct after the irradiation. We developed an algorithm that compared the content of each page and highlighted the page that had a content that did not match with the majority of similar pages.

It was found that one of pages A was corrupted after gamma irradiation (35 kGy) in one tag out of 13 tags. However, because the majority of similar pages had identical data, the overall data was correctly identified. As a result of the redundant data writing onto ferroelectric memory, each tag out of 13 tested tags was correctly read and thus, all tags passed the gamma irradiation test, although one page (80 bytes) was corrupted by gamma radiation.

For another example, the improvement of reliability of writing and reading data onto RFID tags after their gamma irradiation was demonstrated using memory chips MB89R118A (Fujitsu). These memory chips are made using a standard 0.35 micrometers CMOS circuitry coupled with a ferroelectric memory. These memory chips were attached to 5.5×8.5 cm antenna. Details of writing and reading of data and the method of redundancy of writing data was described in the first example.

Before irradiation the read range of the tested RFID tags with memory chips based on CMOS circuitry and ferroelectric memory was from 10 to 50 mm from the reader. It was unexpectedly found that immediately after irradiation with 35 kGy of gamma rays, the read range became very narrow, 20-21 mm from the reader. The read range became 12-30 mm after 2 weeks after gamma irradiation. The read range found after irradiation did not reach the initial read range after months after the irradiation. To read reliably the RFID tags after gamma irradiation the power level of the employed RFID reader was altered from its minimum to its maximum and the tag response was determined. To read reliably the RFID tags after gamma irradiation, the distance between the employed RFID reader and the RFID tag was altered from its minimum to its maximum distance before the tag gamma irradiation and the tag response was determined.

For example 3, the release of additional memory blocks for the end-user after the gamma irradiation was demonstrated after the redundancy of written data was implemented. RFID tags 102 with ferroelectric memory and with redundant data were used as described in Example 1. After the irradiation, the data was read from the memory of ferroelectric memory chips. The correct data was established from the at least three identical pages. Thus, the rest of the pages were released for the end user.

Figure 7:
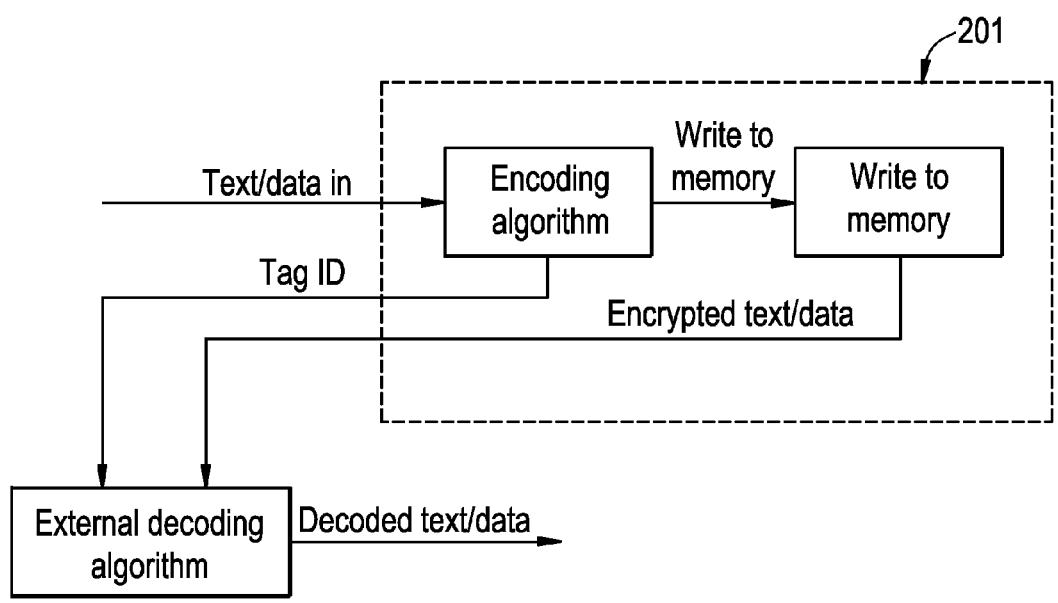
FIG. 7 shows a schematic of an operation of the memory chip of FIG. 3 in accordance with the invention.

Referring to FIG. 7, this figure shows the operation of the memory chip 201. Text or data is written onto the memory chip. Redundant data is written in sequence into the memory of the memory chip 201 using a digital reader/writer 111 (FIG. 1) device for example from Texas Instruments, Wave Logic, etc. Typically, the reader/writer is called a reader. The RFID reader 111 operates with the RFID tag 102 where the RFID tag 102 is composed of the antenna coil 203 and the memory chip 201 (FIG. 3) that includes basic modulation circuitry (on-board rectification bridge and other RF front-end devices) 201*a* and non-volatile memory 201*b*. The tag 102 is energized by a time-varying electromagnetic radio frequency (RF) wave (called a carrier signal) that is transmitted by the reader 111. The reader is a microcontroller-based unit with a wound output coil, peak detector hardware, comparators, and firmware designed to transmit energy to a tag and read information back from it by detecting the backscatter modulation. When the RF field passes through an antenna coil, an AC voltage is generated across the coil. This voltage is rectified by the modulation circuitry of the memory chip 201 to supply power to the tag 102. The information stored in the tag 102 is transmitted back (backscattered) to the reader 111. The reader 111 demodulates the signals received from the tag antenna 203, and decodes the signal for further processing. The memory chip 201 is connected to the tag antenna 203.

During the writing process, an encoding algorithm that is stored on the chip 201 is used to encode the text/data. After encoding (encryption) completion, text/data, the encoded (encrypted text/data) is read from the memory chip 201. It further is directed into an external decoding algorithm that operates in combination with reading of a tag ID value. The tag ID value in combination with the external decoding algorithm produces a decoded text/data.

Referring to FIG. 5, at block 509, the disposable component 101 with an integrated RFID tag 102 is sterilized, such as by radiation sterilization or gamma-sterilization. The gamma sterilization process is described in: Baloda, S.; Martin, J.; Carter, J.; Jenness, E.; Judd, B.; Smeltz, K.; Uettwiller, I.; Hockstad, M., Guide to Irradiation and Sterilization Validation of Single-Use Bioprocess Systems, Part 1, *BioProcess International* 2007, September, 32-40, which is hereby incorporated by reference. Radiation sterilization is a common means of microbial control and sterilization applied to single-use systems. Gamma irradiation is the application of electromagnetic radiation (gamma rays) emitted from radionuclides such as Cobalt 60 (60 Co) and Cesium 137 (137 Cs) isotopes. Gamma rays are not retarded by most materials and can penetrate through most single-use bioprocess system components. Microorganisms are inactivated by damage to their nucleic acids resulting from this ionizing irradiation. Gamma rays are also not retained by material and leave no residual radioactivity. Gamma irradiation dosage is measured in kilogray (kGy) units, which quantify the absorbed energy of radiation. One gray is the absorption of one joule of radiation energy by one kilogram of matter (one kGy=one joule/gram). A conversion from megarad to kilogray is:

1 megarad (Mrad)=10 kilogray, kGy.

The dosages that are greater than or equal to 8 kGy are generally adequate to eliminate low bio-burden levels. In cases where bio-burden level is elevated (>1,000 colony forming units, or cfu, per unit), as may occur with very large single-use systems, higher doses may be required to achieve sterility. Generally, 25 kGy can achieve sterility with a sterility assurance level (SAL) of $10^{-6}$. Even with elevated bio-burden levels, reduction can be achieved with lower probabilities of sterility (e.g., SAL of $10^{-5}$ or $10^{-4}$). Products irradiated to such SALs are still sterile but have higher probabilities of non-sterility and may not meet standards for validated sterile claims as specified in industry standards for sterilization of health care products. The gamma irradiation process uses well-defined operating parameters to ensure accurate dosing. In a well-designed irradiation facility, for any given density of material the only variable determining the amount of radiation the product and microorganism receives is the time the material spends within the radiation field. Products are not exposed to heat, humidity, pressure, or vacuum. Gamma irradiation produces minimal waste byproducts and does not require quarantine for out-gassing (as with ethylene oxide gas sterilization) or routine biological reactivity testing. As a constant and predictable sterilization method, gamma irradiation provides benefits in safety, time, and cost.

Next, at block 511 the disposable component 101 is assembled in a biological fluid flow. Disposable bioprocess component 101, for example may be storage bags, bioreactors, transfer lines, filters, separation columns, connectors, and other components, are assembled using acceptable common practices and manufacturing approaches known to those of ordinary skilled in the art.

At block 513, there is a determination if the disposable component 101 (FIG. 1) is authentic. The reader 106 of the measurement device 111 is utilized to authenticate the RFID tag 102 of the disposable component 101. Authentication is performed to prevent illegal use of the disposable bioprocess components, to prevent illegal operation of the disposable bioprocess components, and to prevent illegal pharmaceutical manufacturing. There is a need to authenticate products in supply chain applications because counterfeits can be very similar or even identical to authentic products. As described in Lehtonen, M.; Staake, T.; Michahelles, F.; Fleisch, E., From Identification to Authentication—A Review of RFID Product Authentication Techniques, In *Networked RFID Systems and Lightweight Cryptography. Raising Barriers to Product Counterfeiting;* P. H. Cole and D. C. Ranasinghe, Ed.; Springer: Berlin Heidelberg, 2008; 169-187, which is hereby incorporated by reference, RFIDs are employed for product authentication. The benefits of RFID compared to old authentication technologies include non line-of-sight reading, item-level identification, non-static nature of security features, and cryptographic resistance against cloning. RFID systems in general comprise RFID tags, readers, and online database.

Product authentication using RFIDs can be based on RFID tag authentication or identification and additional reasoning using online product data. Furthermore, RFID supports for secure ways to bind the RFID tag and the product. To resist cloning and forgery are the most important security properties of authentication RFID tags.

There are several RFID product authentication approaches. One product authentication approach is unique serial numbering. By definition, one of the fundamental assumptions in identification, and thus also in authentication, is that individual entities possess an identity. In supply chain applications, issuing unique identities is efficiently accomplished with RFID. There is a unique serial numbering and confirmation of validity of identities as the simplest RFID product authentication technique. The simplest cloning attack against an RFID tag 102 only requires the reader 106 reading the tag serial number and programming the same number into an empty tag. However, there is an essential obstacle against this kind of replication. RFID tags have a unique factory programmed chip serial number (or chip ID). To clone a tag's ID would therefore also require access to the intricate process of chip manufacturing.

Another product authentication approach is track and trace-based plausibility check. Track and trace refers to generating and storing inherently dynamic profiles of individual goods when there is a need to document pedigrees of the disposable bioprocess product, or as products move through the supply chain. The product specific records allow for heuristic plausibility checks. The plausibility check is suited for being performed by customers who can reason themselves whether the product is original or not, though it can also be automated by suitable artificial intelligence. Track and trace is a natural expansion of unique serial numbering approaches. Furthermore, track and trace can be used in supply chains for deriving a product's history and for organizing product recalls. In addition, biopharmaceutical industry has legislation that demands companies to document product pedigrees. Therefore, the track and trace based product authentication can be cost-efficient, as also other applications to justify the expenses.

Another product authentication approach is secure object authentication technique that makes use of cryptography to allow for reliable authentication while keeping the critical information secret in order to increase resistance against cloning. Because authentication is needed in many RFID applications, the protocols in this approach come from different fields of RFID security and privacy. In one scheme, it is assumed that tags cannot be trusted to store long-term secrets when left in isolation. Thus, the tag 102 is locked without storing the access key, but only a hash of the key on the tag 102. The key is stored in an online database of the computer 109 connected to the reader 106 and can be found using the tag's 102 ID. This approach can be applied in authentication, namely unlocking a tag would correspond authentication.

Another product authentication approach utilizes product specific features. In this approach the authentication is based on writing on the tag 102 memory 201 a digital signature that combines the tag 102 ID number and product specific features of the item that is to be authenticated. These product specific features of the item that is to be authenticated can be response of the integrated RFID sensor. The sensor is fabricated as a memory chip with an analog input from a separate micro sensor. The sensor also can be fabricated as described in U.S. patent application numbers US 2007-0090926, US 2007-0090927, US 2008-0012577, which are hereby incorporated by reference. These features can be physical or chemical properties that identify the product and that can be verified. The chosen feature is measured as a part of the authentication by the reader 106 and if the feature used in the tag's signature does not match the measured feature, the tag-product pair is not original. This authentication technique needs a public key stored on an online database that can be accessed by the computer 109 connected to the measurement device 111. An offline authentication can be also used by storing the public key on the tag 102 that can be accessed by the computer 109 connected to the measurement device, though this decreases the level of security.

Gamma resistant RFID tag 102 facilitates the authentication of the disposable component onto which it is attached. Authentication involves verifying the identity of a user logging onto a network by using the measurement device 111 and the reader 106 and the disposable component or assembled component system. Passwords, digital certificates, and smart cards can be used to prove the identity of the user to the network. Passwords and digital certificates can also be used to identify the network to the client. The examples of employed authentication approaches include: Passwords (What You Know) and Digital certificates, physical tokens (What You Have, for example integrated RFID sensor with its response feature); and their combinations. The use of two independent mechanisms for authentication; for example, requiring a smart card and a password is less likely to allow abuse than either component alone.

One of the authentication approaches using the gamma resistant RFID tag 102 on the disposable component 101 involves mutual authentication between reader 106 and RFID tag 102 which is based on the principle of three-pass mutual authentication in accordance with ISO 9798-2, in which a secret cryptographic key is involved. In this authentication method, the secret keys are not transmitted over the airways, but rather only encrypted random numbers are transmitted to the reader 106. These random numbers are always encrypted simultaneously. A random session key can be calculated by the measurement device 111 and the reader 106 from the random numbers generated, in order to cryptologically secure the subsequent data transmission.

Another authentication approach is when each RFID tag 102 has a different cryptological key. To achieve this, a serial number of each RFID tag 102 is read out during its production. A unique key is further derived using a cryptological algorithm and a master key, and the RFID tag 102 is thus initialized. Thus, each RFID tag 102 receives a key linked to its own ID number and the master key.

RFID tags with unique serial numbers can be authenticated and also access lot information (e.g. date of manufacture, expiration date, assay results, etc.) from the device manufacturer. The serial number and lot information is transferred to a user accessible server once the product has been shipped. The user upon installation then reads the RFID tag that transmits the unique serial number to a computer with a secure interne link to the customer accessible server. A match of the serial number on the server with the RFID tag serial number then authenticates the device and permits use of the device. Once the information is accessed on the server the information is then becomes user inaccessible to prevent reuse of a single use device. Conversely, if there is no match with a serial number the device cannot be used and is locked out from authentication and access of lot information.

To encrypt data for its secure transmission, the text data is transformed into encrypted (cipher) text using a secret key and an encryption algorithm. Without knowing the encryption algorithm and the secret key, it is impossible to recreate the transmission data from the cipher data. The cipher data is transformed into its original form in the receiver using the secret key and the encryption algorithm. Encryption techniques include private key cryptography and public key cryptography that prevent illegal access to internal information in the memory on the memory chip.

If it is determined that the disposable component 101 is not authenticated then at block 515, the disposable component 101 has a failure. If there is a failure with the disposable component 101, then the user is warned that the disposable component 101 does not appear to be authenticated or genuine and should be investigated. A failure can (1) generate a visual or audible alarm, (2) send a message to the data-base provider; (3) halt execution of the process. However, if the disposable component 101 is authenticated and has passed at block 517 then the operation is allowed. If it is allowed then the disposable component 101 is genuine and the performance of the task is genuine. By ensuring that only approved disposable components 101 are used, there is a reduction in the liability that a counterfeit poor quality disposable component 101 is used on the hardware and a user files an unjustified complaint or those processes which were not granted export use license by government authorities are prohibited.

Next, at block 519 user critical digital data at the disposable component 101 is released and the process ends. The disposable component 101 will also allow users to access manufacturing information about the product—for example lot number, manufacturing data, release specifications etc. This data would only be available if the card reader 106 was able to verify the RFID tag 102 was authentic and genuine. This user critical data will be displayed on the computer 109, which also may be connected to a typical printer, such as HP LaserJet 1200 Series manufactured by Hewlett Packard, 3000 Hanover Street, Palo Alto, Calif. 94304 that prints this release data.

This invention provides a system and apparatus that is able to authenticate and prevent illegal pharmaceutical and other manufacturing and unauthorized operation of disposable bioprocess components. This invention utilizes a ferro-electric random access memory chip (FRAM) chip to store redundant information on a RFID tag attached to the disposable bioprocess components, where the redundant information is written in sequence into the memory chip, so that the redundant information can remain in the chip when the RFID tag and disposable bioprocess component is gamma-sterilized. Also, this invention includes a method for authenticating the disposable bioprocess component that reduces liability in that a counterfeit poor quality disposable component is not used on the hardware so the user will not file an unjustified complaint.

It is intended that the foregoing detailed description of the invention be regarded as illustrative rather than limiting and that it be understood that it is the following claims, including all equivalents, which are intended to define the scope of the invention.

What is claimed is:

1. A method of authenticating a component to confirm the component is suitable for use, the method comprising:
   receiving a component having a radio-frequency identification (RFID) device attached thereto, the RFID device including memory having redundant authentication information therein, wherein the component and the RFID device have been sterilized using radiation, at least one region of the memory being corrupted by the radiation;
   obtaining multiple readings of the memory, including data from the at least one region corrupted by the radiation, the multiple readings being obtained by an RFID reader that at least one of (a) uses different power levels to read the memory or (b) is located at different distances from the RFD device when the memory is read;
   analyzing the multiple readings to determine the authentication information; and
   authenticating the component using the authentication information to confirm that the component is suitable for use, wherein authenticating includes analyzing or processing the authentication information in a predetermined manner.

2. The method of claim 1, wherein the memory includes a ferroelectric random memory (FRAM).

3. The method of claim 1, wherein the memory includes non-charge-based storage memory.

4. The method of claim 1, wherein the RFID device includes an RFID tag.

5. The method of claim 1, wherein the RFID device includes an RFID sensor.

6. The method of claim 1, wherein receiving the component having the RFID device attached thereto includes sterilizing the component and the attached RFID device using gamma irradiation with a dose in the range from 5 to 100 kGy.

7. The method of claim 1, wherein the error-correctable information is redundant information written to a plurality of regions of the memory.

8. The method of claim 1, wherein the memory includes multiples copies of the error-correctable information at different regions of the memory including the at least one region corrupted by the radiation.

9. The method of claim 8, wherein analyzing the multiple readings includes identifying the at least one region that is corrupted by the radiation by comparing data from the other regions.

10. The method of claim 8, wherein analyzing the multiple readings includes determining that data of the at least one region corrupted by the radiation is different than data of the other regions.

11. The method of claim 1, wherein the memory is part of a memory chip including a CMOS portion and a FRAM portion, wherein the at least one region corrupted by radiation is part of the FRAM portion.

12. The method of claim 1, wherein authenticating the component using the authentication information includes at least one of: (a) using identification information that identifies the component or is uniquely associated with the component; (b) using a track-and-race plausibility check; (c) determining a pedigree of the component; (d) using a crypographic or cryptological key; or (d) matching a serial number of the component.

13. A method of authenticating a component to confirm the component is suitable for use, the method comprising:
   receiving a component havin a radio-frequency identification (RFID) device attached thereto, the RFID device including memory having redundant authentication information therein, wherein the bioprocess component and the RFID device have been sterilized to reduce bioburden, at least one region of the memory being corrupted by the sterilization;
   obtaining multiple readings of the memory, including data from the at least one region corrupted by the sterilization, the multiple readings being obtained by an RFID reader that at least one of (a) uses different power levels to read the memory or (b) is located at different distances from the RFID device when the memory is read;
   analyzing the multiple readings to determine the authentication information; and
   authenticating the component using the authentication information to confirm that the component is suitable for use, wherein authenticating includes analyzing or processing the authentication information in a predetermined manner.

14. The method of claim 13, wherein the sterilization includes radiation exposure.

15. The method of claim 13, further comprising releasing user-critical data from the RFID device after authenticating the bioprocess component.

16. The method of claim 13, where in the user-critical data includes manufacturing information associated with the bioprocess component.

17. The method of claim 13, wherein the bioprocess component is a disposable bioprocess component.

18. The method of claim 13, wherein the memory portion includes complementary metal-oxide semiconductor (CMOS) circuitry.

19. The method of claim 13, wherein the memory includes ferroelectric random memory (FRAM).

20. The method of claim 19, wherein the FRAM includes a plurality of sectors.

21. The method of claim 20, wherein a first sector of the plurality of sectors includes article identification information or a serial number.

22. The method of claim 13, wherein the bioprocess component is selected from the group consisting of a stainless steel container, a bioreactor, a plastic container, a polymeric material container, a chromatography device, a filtration device and a centrifuge device, 23. The method of claim 13, wherein the memory includes multiples copies of the authentication information at different regions of the memory including the at least one region corrupted by the sterilization.

24. The method of claim 23, wherein analyzing the multiple readings includes identifying the at least one region that is corrupted by the sterilization by comparing data from the other regions.

25. The method of claim 23, wherein analyzing the multiple readings includes determining that the data of the at least one region corrupted by the sterilization is different than data of the other regions.

26. The method of claim 13, wherein the memory is part of a memory chip including a CMOS portion and a FRAM portion, wherein the at least one region corrupted by sterilization is part of the FRAM portion.

* * * * *